United States Patent [19]
Thilly

[11] Patent Number: 6,012,595
[45] Date of Patent: Jan. 11, 2000

[54] STORAGE DEVICES

[75] Inventor: Jacques Thilly, Brussels, Belgium

[73] Assignee: SmithKline Beecham Biologicals s.a., Rixensart, Belgium

[21] Appl. No.: 08/464,703

[22] PCT Filed: Dec. 21, 1993

[86] PCT No.: PCT/EP93/03665

§ 371 Date: Aug. 2, 1995

§ 102(e) Date: Aug. 2, 1995

[87] PCT Pub. No.: WO94/14484

PCT Pub. Date: Jul. 7, 1994

[30] Foreign Application Priority Data

Dec. 24, 1992 [GB] United Kingdom .................... 9226955

[51] Int. Cl.⁷ ........................................................ A47F 1/04
[52] U.S. Cl. ............................................................ 211/60.1
[58] Field of Search ........................... 211/60.1, 74, 113, 211/70.6

[56] References Cited

U.S. PATENT DOCUMENTS

| | | | |
|---|---|---|---|
| 2,313,905 | 3/1943 | Wallin | 211/69 |
| 3,220,558 | 11/1965 | Olsson | 211/74 |
| 4,022,363 | 5/1977 | Eliassen | 211/74 X |
| 4,037,766 | 7/1977 | Iacono | 224/45 |
| 4,142,633 | 3/1979 | Raghavachari et al. | 206/366 |
| 4,273,416 | 6/1981 | Blum | 211/74 |
| 4,350,253 | 9/1982 | Rusteberg | 211/74 |
| 4,863,020 | 9/1989 | Klemov | 211/113 |
| 4,932,533 | 6/1990 | Collier | 206/569 |
| 5,169,603 | 12/1992 | Landsberger | 422/104 |
| 5,386,915 | 2/1995 | Sirhan | 211/70.6 |
| 5,598,924 | 2/1997 | McCann | 211/70.6 X |

*Primary Examiner*—Alvin Chin-Shue
*Assistant Examiner*—Sarah Purol
*Attorney, Agent, or Firm*—Zoltan Kerekes; Stephen Venetianer; Charles M. Kinzig

[57] ABSTRACT

For storage of syringes, a support rack comprising a plurality of elongate fingers (2) connected together at one end by a spine member (1) is used. The fingers (2) define parallel support channels (5) open at one end, and the syringes are stored in the channels (5) with their lips or wings (4) resting on the elongate fingers (2). Also disclosed are support cradles, storage boxes, and lifting devices for handling the loaded racks. The support rack is better adapted than existing systems for cooperation with automated machinery since it can receive syringes into the channels by a horizontal translation movement, readily provided by a simple pushing device.

11 Claims, 8 Drawing Sheets

STORAGE DEVICES

The present invention relates to various cooperating devices for storing lipped or winged articles, especially cylindrical articles such as syringes.

Many containers for liquids, particularly those made from glass, are, by virtue of their purpose, of such a shape that they are not easily storable and as such many are often broken or damaged during processing—filling, quality control, labelling and packaging for example.

Glass syringes, in particular, suffer from these disadvantages. Furthermore, they also have protruding glass wings which can easily crack under shock, and are often supplied with a needle attached which can bend under pressure.

For sterilisation processes, it has been proposed to secure one or more rows of syringes to stainless steel rail-trays, supporting the wings on the rails. These rail-trays can subsequently be used to support the syringes during filling.

In another conventional technique, glass syringes may be vertically stored and filled whilst resting in a hole and being supported by its wings. Generally, a number of syringes are supported in a matrix of holes in a nest held in a tub formed from plastics material (for example, the Becton-Dickinson SCF system). Once filled with the appropriate liquid, the syringe have to be inspected individually for particulate contamination, which for careful examination necessitates removal of the syringe from the nest.

Syringe bodies may also be stored and removed from nests for operations such as insertion of plungers, labelling and final packing.

Automated removal requires either grasping of the syringe from above by a robot and thereby risking cracking the glass, or pushing of the needle from below and thereby risking damage to the needle. As such it is preferable for this removal and replacement to be carried out manually. As a result of this fragility, on production lines where syringes are filled and packaged it is difficult to achieve a throughput of greater than 6000 syringes per man hour in removing syringes from the nest and just 4000 per man hour in replacing syringes.

As the filling, insertion of the syringe plunger, labelling and packaging processes occur at differing rates either the whole process runs as a single continuous process, running at the rate of the slowest individual procedure, or the syringes must be removed from the tub, processed and then returned to the tub for intermediate storage at every stage in the production of a filled syringe. These different operations may be carried out at different locations of a production facility. All this results in further opportunities for the occurrence of damage to the syringe or needle during transfer. It is therefore preferred to run the whole process as a single continuous procedure. However, this results in a further problem in that whenever an individual procedure comes to a standstill, due to a machine breaking down for example, the whole process is also stopped. Alternatively complex buffer devices, such as spiral racks, are needed to absorb continuous production.

There is a need therefore for the development of a system whereby glass syringes can be conveniently stored and moved from one process to another with a reduced risk of damage thereto, with the system being of low cost (for example by using injection moulding) and requiring a reduced labour involvement.

The present invention is based on the use of a support rack for storage of lipped or winged articles, especially cylindrical articles such as syringes. The support rack comprises a plurality of elongate fingers connected together at one end by a spine member, the fingers thereby defining parallel support channels open at one end. The articles are located in the channels with their lips or wings resting on the elongate fingers.

The support rack itself forms one aspect of this invention.

Generally the fingers extend from one side only of the spine. Therefore the support rack typically has a generally comb-like appearance with the teeth of the comb defining the open-ended channels.

The articles may be placed in the channels from above as in existing nest systems, or more preferably by sliding through the open end of each channel. The articles rest in the channels with their lips or wings supported by the fingers (or teeth).

The support rack is better adapted than existing systems for cooperation with automated machinery since it can receive articles into the channels by a horizontal translation movement, readily provided by a simple pushing device.

The "comb" may be conveniently moulded in one piece from plastics material, such as polystyrene.

In another aspect of the invention the support rack may be provided with a support body or cradle to allow a support rack to be stored with articles loaded thereon in a generally upright fashion. The cradle comprises a base having extending upwardly therefrom means for supporting the "comb". The comb is supported above the base so as to allow articles such as syringes to hang via their wings or lips supported on the fingers of the comb, without the articles contacting the base. The supporting means may be in the form of a plurality of support posts, preferably including a post under the end of each elongate finger in order to keep their positions steady during the various operations such as loading and unloading. Preferably the support posts are disposed around the periphery of the base.

In a further aspect of the invention, for transfer of the comb, there may be provided a carrying handle comprising a handle portion and two or more comb-engaging means. This allows for safe transfer of loaded comb between cradle and storage box. Typically, two engaging means cooperate respectively with opposed ends of the comb, preferably the spine and the free ends of the fingers. Preferably at least one of the engaging means is movable by a pivoting or sliding motion between a first position wherein the engaging means engage the comb; and a second position wherein the engaging means are out of engagement with the comb. The engaging means may include a flange to support the comb from the underside face thereof, or may have projections that cooperate with recesses provided in the outer-facing edges of the spine member and elongate fingers. A grip may be provided on the carrying handle to allow the comb to be lifted by means of the handle when the engaging means engage the comb.

In a yet further aspect of the present invention there is provided a storage box comprising a base portion and a cover portion at least one of which portions has an internal shelf or ledge having a plurality of projections extending therefrom, the projections in use, engaging the open end of the comb channels to restrain the fingers from lateral movement; and wherein the base portion and cover portion cooperate to restrain vertical movement of the comb. When syringes have been previously stored using the Becton-Dickinson SCF system, the base portion may conveniently be an existing or conventional Becton-Dickinson tub, so that the channel-engaging protrusions are provided in the cover portion.

In another aspect the present invention provides apparatus for transferring syringes to and from a storage rack comprising:

a loading channel for receiving syringes from or for a processing operation, means for transporting a syringe support rack of this invention to a position where an end channel of the support rack is in alignment with the loading channel, means for urging syringes from the loading channel into the support rack channel or vice versa, means for indexing the transporting means to bring the next free support rack channel into alignment with the loading channel.

In transfer of syringes into a support rack, preferably a counter is provided so that syringes can be retained in the loading channel when a rack channel has been filled and indexing is taking place. Therefore in a preferred embodiment, the apparatus includes:

means for counting syringes entering the loading channel, means for preventing syringes leaving the loading channel until a predetermined number of syringes are in the channel, means for preventing syringes entering the loading channel after a predetermined number of syringes are in the channel, means for urging the predetermined number of syringes from the loading channel into the support rack channel.

Typically, syringes exiting from, for example a labelling or filling apparatus, are counted, for example by breaking a light beam, as they enter a loading channel comprising two elongate beams on which the syringes are supported by their wings. Spaced barriers moveable across the channel by a signal from the counter isolate a group of syringes capable of fitting in one channel of the syringe support rack.

The syringe support rack may be mounted on the support cradle of the invention and carried by a conveyor to a position where its syringes can be transferred by a pusher arm from the loading channel to the storage channel. After all storage channels are filled, the conveyor may remove the cradle and loaded support rack from the loading site while transporting an empty support and cradle into the loading position.

For loading syringes into a processing apparatus, a filled support rack may similarly be conveyed to a syringe loading channel and indexed into alignment. The syringes can be transferred manually or by an automated pusher arm from the support into the loading channel, from which they are transported conventionally into the apparatus for processing.

Embodiments of the present invention will be described in further detail, by way of example, with reference to the accompanying drawings, in which.

Figure 1:
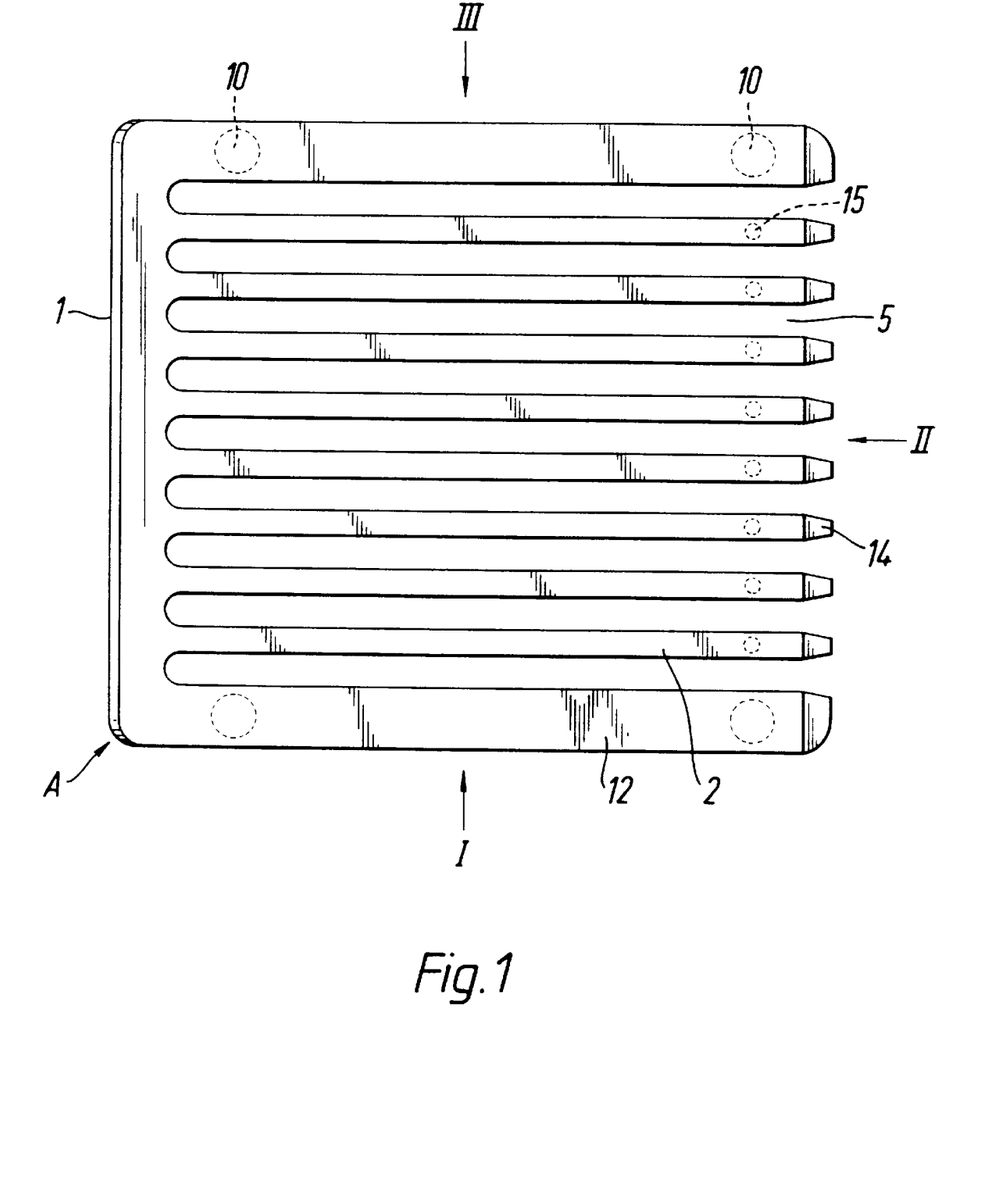
FIG. 1 illustrates in plan view a support rack in accordance with the present invention.

As illustrated in FIG. 1, a support rack in accordance with the present invention comprises a spine portion 1 having extending therefrom a plurality of planar parallel projections 2 to form a generally comb-shaped apparatus (shown generally as comb A). In use, an elongate article such as a syringe 3 may be easily slid into position in a channel 5 defined by two adjacent projections 2 and being of slightly greater dimension than the diameter of the syringe. The syringe is supported in place by conventional wings 4 forming part of the syringe body. Preferably the forward tips of the projections 2 are profiled so as to urge a syringe contacting the tip into a channel 5. Suitably this profile is provided in the form of a conical or tapered tip 14.

The embodiment shown provides nine channels each dimensioned to receive fourteen 1 ml syringe bodies (of approximately 10 mm diameter). Using the same external dimensions a comb may be made with ten channels, each receiving fifteen 0.5 ml syringes (approximately 8 mm diameter).

Figure 1A:
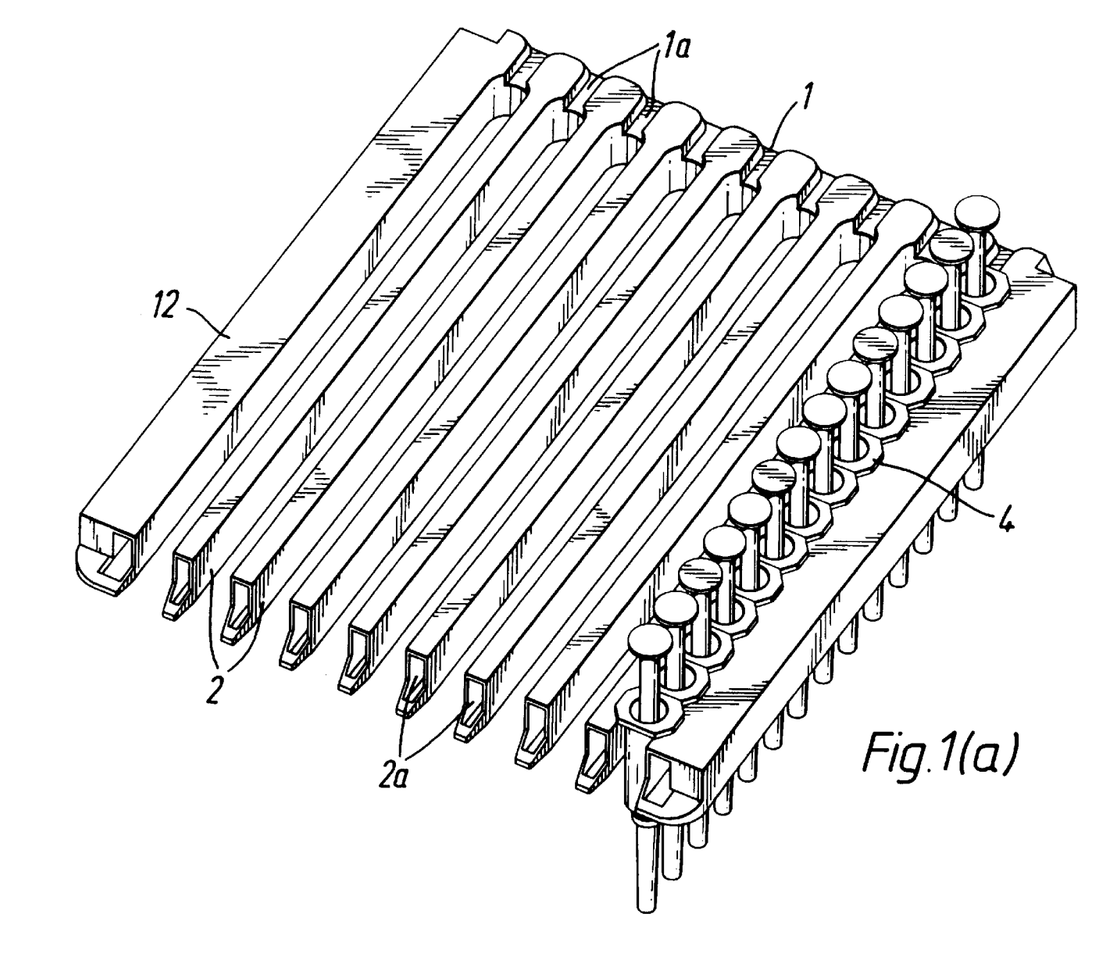
FIG. 1(a) is a perspective view showing the shape and configuration of a preferred support rack and illustrating the storage of syringes.

FIG. 1(a) shows how the support rack may be formed as a partly hollow moulding with inverted channel-shaped projections or fingers 2 extending from spine 1, also formed as an inverted channel. The upper surface of each finger 2 is planar and of sufficient width that the wings or lips of stored articles in adjacent channels do not contact each other so as to impede loading or unloading. Preferably the upper surface of each finger 2 is higher than the upper surface of spine 1 so that a small channel 1a is formed on the spine between each finger. This allows cooperation with retaining lugs on a lid of a storage box as described later. Apertures 2a cut into the inverted channels at the free end of the fingers 2 allows insertion of a lifting device even when the rack is stored in a box, again as described later.

Figure 2:
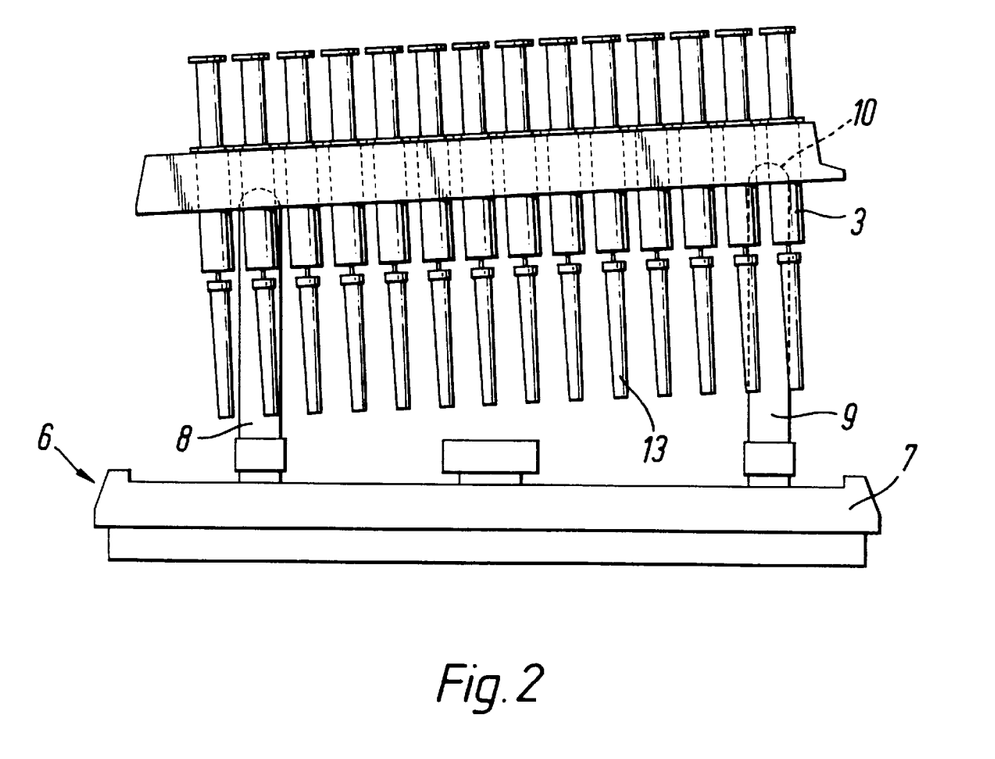
FIG. 2 illustrates a view from side I in FIG. 1 of the support rack of FIG. 1 with associated support cradle.

In a fully loaded state it is necessary to support the comb. This may be achieved by a support cradle shown generally at 6. The support cradle 6 comprises a base 7 itself supportable on a conventional palette appropriate to the conveyor system in use. The base 7 has extending upwardly therefrom a plurality of support posts 8,9 disposed around the outer portions of the base such that in use the posts do not interfere with the loading of the syringes onto the comb. As shown in FIGS. 1 and 2 it may be preferable to use just four such posts 8 and 9 positioned in a square configuration. The upper end of each post (remote from the base) locates in a depression 10 on the underside of the comb A. For convenience it may be preferable to provide such depressions on both faces of the comb such that the comb may be used in either orientation. For added strength and to provide space for location of the means for supporting the comb, the two outer projections 12 may be wider than the remaining inner projections 2.

In the embodiment shown in FIG. 1(a), the posts may simply locate within the inverted channels of the fingers 2. The broader channels 12 may need to contain internal stiffening ribs. In that case the depressing the he formed by decreasing the height of the ribs at the appropriate point, for example forming semi-circular cut-outs in two crossing ribs.

Additionally, as illustrated in FIG. 2, it is advantageous to provide that the front pair of posts 9 remote from the spine member 1 are of greater height than those posts 8 adjacent the spine. It is thus provided that in use on a horizontal surface the comb will be inclined and the syringes will be biased by gravity into a position whereby dislocation of the syringes from the comb will be prevented. This also reduces the risk of dislocation when the palette is not on a horizontal surface.

Towards the front of the base 7 are provided a number of further support posts 11 each of which locates in a depression 15 on the underside of each inner projection 2, thereby providing additional support and stability for the apparatus.

Figure 3:
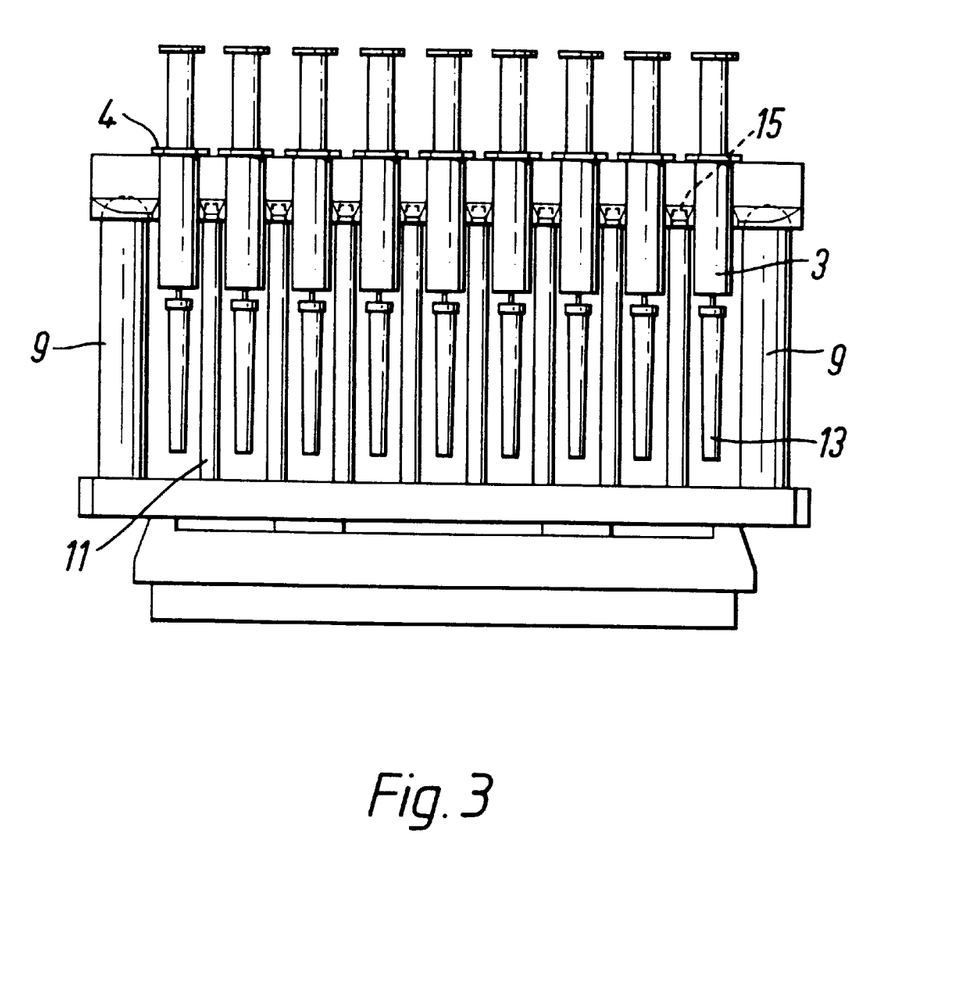
FIG. 3 illustrates a view from the front (side II in FIG. 1) of the support rack of FIG. 1 with associated cradle.
Figure 4:
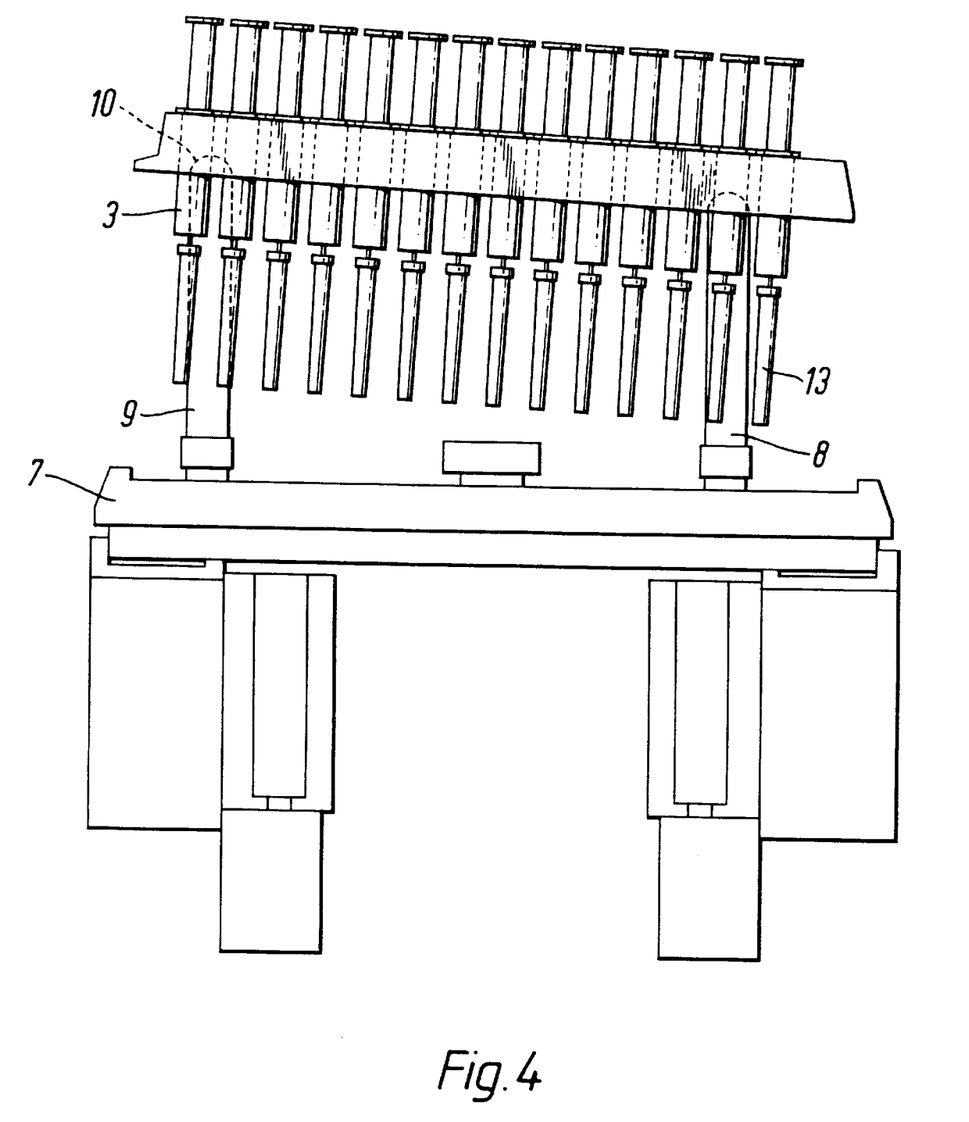
FIG. 4 illustrates a view from side III in FIG. 1 of the support rack of FIG. 1 with associated cradle in position on a conventional conveyor.

As is shown in FIGS. 2–4, when supported on posts 8,9,11 there is sufficient clearance between the comb A and the base 7 to allow for a hypodermic needle 13 attached to the tip of each syringe. Posts 8,9 may be removably secured to the base 7 to allow for the interchange of posts of varying lengths depending upon the length of hypodermic needle attached.

Figure 5:
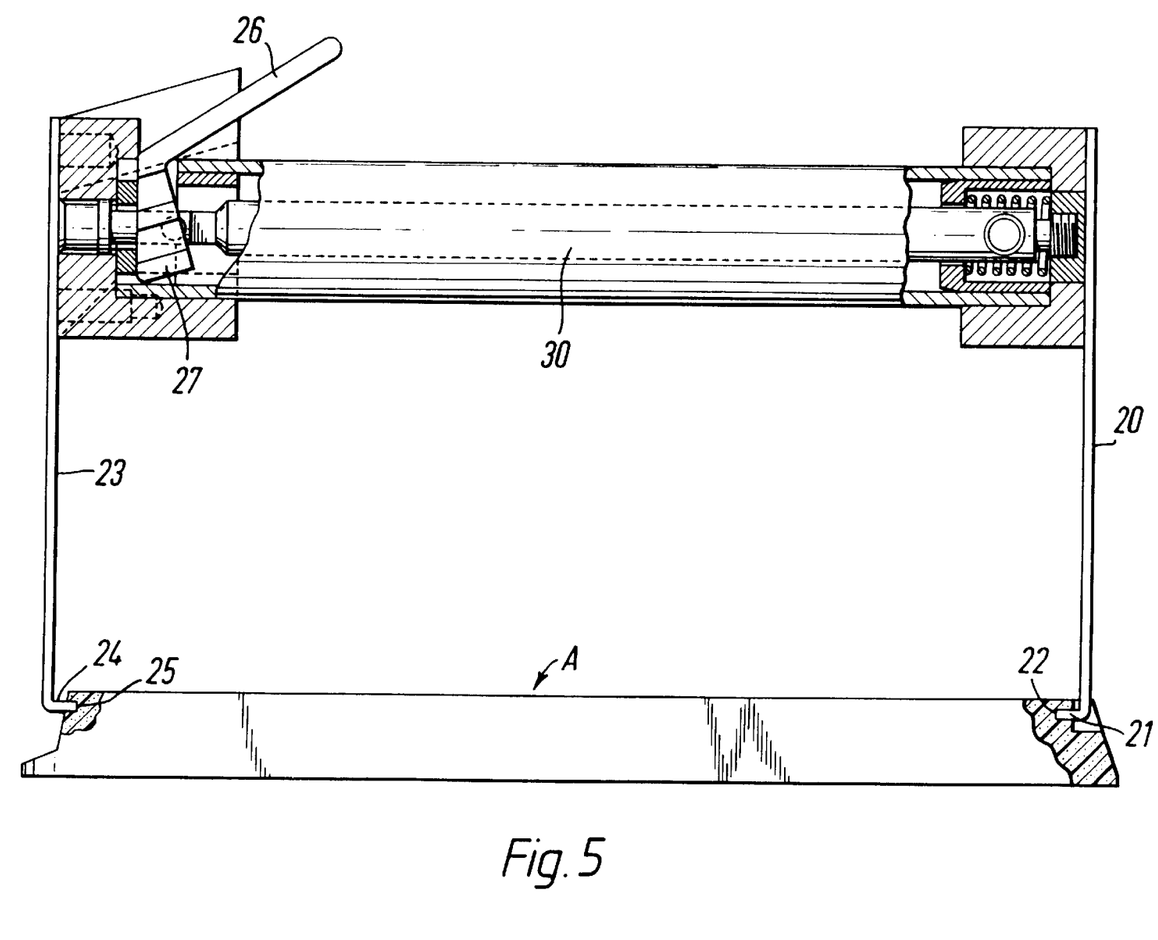
FIG. 5 illustrates a side view of an embodiment of a carrying device for transporting the support rack of the present invention.

FIG. 5 illustrates a carrying handle suitable for transferring a loaded comb A from one processing area to another without the need for transfer of the associated support cradle 6. The handle as shown is suitable for manual transfer, although such a device can be adapted for incorporation into an automated system. The handle illustrated comprises engaging means in the form of a back plate 20 and a front plate 23 attached at their upper edges to a grip 30 and having lips 21,24 at their lower edges. The lip 21 of the back plate 20 is locatable in recess 22 provided in the outward facing edge of spine member 1. The lip of the front plate 23 is in the form of teeth 24 each being locatable in a depression 25 provided in the forward edge of each elongate finger 2,12. Alternative embodiments may provide that the lip 21 of the back plate is also in the form of two or more teeth. The embodiment shown engages the comb by means of front plate 23 which is movable relative to grip 30 in response to movement of lever 26 between a first position wherein teeth 24 are located in depressions 25, and a second position where in the teeth are out of engagement with the depressions. In this embodiment the back plate 20 is fixed. The plate 23 is biassed into the first position, for example by a spring connected to the grip 30. Lever 26 is pivotably mounted so that downward movement of the lever 26 moves the reaction member 27, connected to the lever 26, into contact with the plate 23, or a connected reaction plate, to move the plate 23 into the second position against the spring bias. The handle is positioned over the support rack with the plate 20 adjacent or engaged with the spine of the support rack. Release of the lever 26 allows the plate 23 to move into engagement with the free ends of the support fingers, while pressing the spine into firm engagement with the back plate 20.

Alternative systems could comprise a fixed front plate and movable back plate or both plates could be movable.

In use, syringes can be easily and safely slid into position in the comb A whereby each syringe is supported by its wings resting on projections 2,12. The body of the syringe (either with or without a hypodermic needle being attached) extends downwardly through the opening 5. As the syringes proceed through each individual step of the filling, quality control, labelling and packaging procedure, the syringes may be loaded into the appropriate machine by simply sliding them off the comb. By allowing for the syringes to slide in and out of the comb, the risk of damage caused by inserting and removing syringes by grasping the syringe body or pushing the needle as required by existing storage devices is considerably reduced. It is therefore no longer essential to run all the individual steps as a continuous process. Upon completion of a single task, a comb is reloaded, again by sliding the syringes into place, and can be stored in a buffer zone, ready for the next step.

Figure 6A:
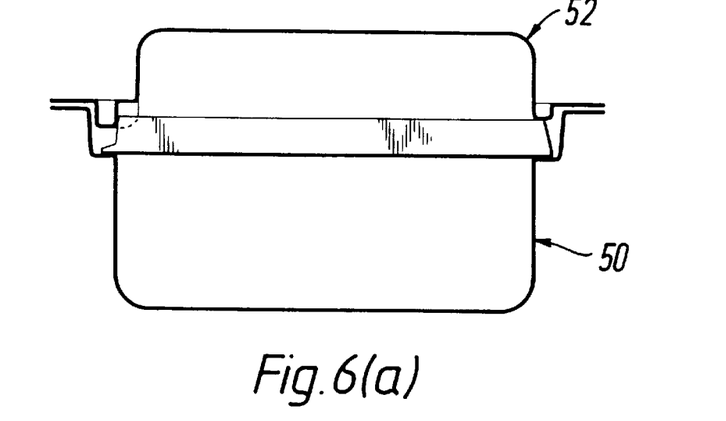
FIGS. 6(a)&(b) illustrate an embodiment of the storage cover of the present invention, FIG. 6(a) being a cross-sectional view and FIG. 6(b) being a detail of the restraining means.

A loaded comb is preferably stored in such a manner as to prevent movement of the fingers 2,12 in the event of accidental movement of the comb, and thereby reduce the risk of damage to the stored articles. Safe storage may be effected as shown in FIG. 6 by the use of a conventional box 50 having an internal support shelf 51 and a cover 52 having a corresponding internal securing ledge 53 which,in use, cooperates with support shelf 51 to secure a comb placed on the support shelf and thereby prevent vertical movement of the comb. Cover 52 has projections 54 along one internal edge which, in use, engage with fingers 2,12 of a comb supported on shelf 51. The protrusions prevent lateral movement of the fingers and also to block the channels 5 to prevent horizontal movement of stored syringes, wedging stored syringes into close contact with each other. Similar projections at the other end of the cover may engage with the channels 1a shown in FIG. 1(a).

Alternatively, a box may be provided wherein one of the shelves 51 incorporates the projections. The cover then acts to prevent vertical movement of the comb.

Figure 6B:
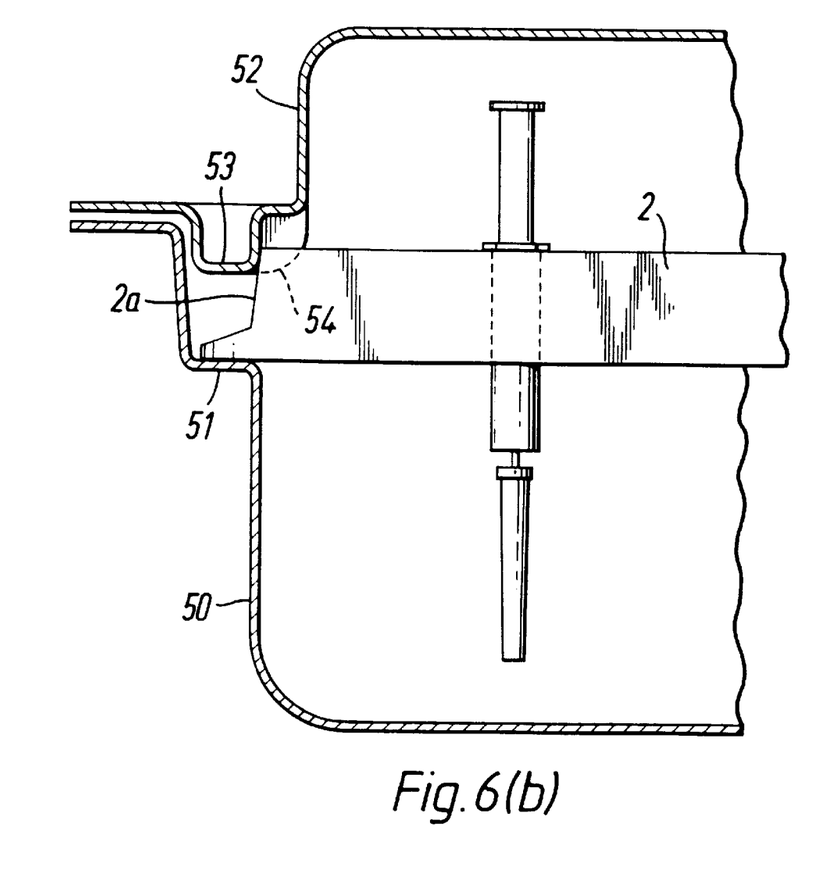
Figure 7:
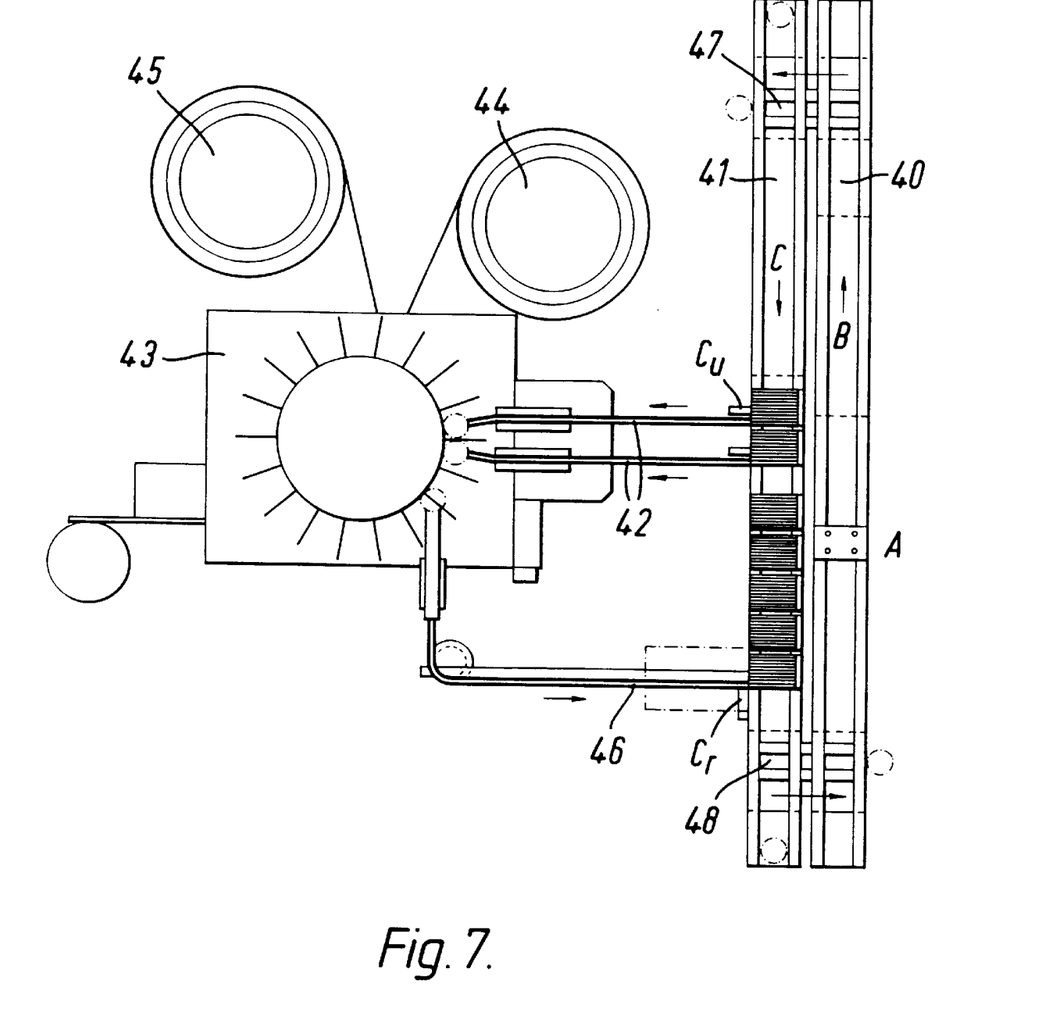
FIG. 7 illustrates, in plan view, a syringe processing machine associated with syringe transfer apparatus in accordance with the present invention.

As can be seen in FIG. 6 (b), the portions 2(a) cut out of the end of the fingers 2, allows insertion of teeth 24 of a lifting device even when the rack is stored in box 50. The support rack and associated devices of this invention may be used to advantage in various syringe processing operations. FIG. 7 shows a machine for labelling syringes and inserting plungers into syringe bodies, and use of a comb loading/unloading system of the present invention. Loaded combs enter the system mounted on a cradle (as described above) along conveyor 41. Combs are unloaded at $C_u$ by pushing syringe bodies down channels 42. The syringe bodies enter a carousel 43 which moves the bodies into position to receive plungers and labels from supply stations 44, and 45. The syringes are then returned to the conveyor 41 at $C_r$ to be reloaded onto a comb to proceed to a packaging or storage area.

Referring in more detail to the unloading/loading system, an operator at position A removes a loaded comb from a stock pile (each in a container as in FIG. 6a/b) and places the comb on a cradle (as shown in FIGS. 2 and 3) running empty on the conveyor 40. The open ends of the storage channels of the comb face towards the apparatus 43. The cradle is moved by the conveyor 40 in the direction B until it reaches transfer section 47. Here transverse belts move the loaded cradle (maintaining its orientation) on to conveyor 41 where it moves in direction C towards apparatus 43. The loaded cradle is followed by further cradles loaded by the operator at A.

The first loaded cradle moves on until it is detected to be at position $C_u$ with the leading channel of the comb level with the second of the two entry channels 42 of the apparatus 43. The first cradle is restrained in that position and the following cradle is restrained in a similar relationship to the other entry channel. The syringes in the support channels aligned with the entry channels can now be pushed manually or by a pneumatically operated pusher arm so that they are transferred into the entry channels 42, from where they are conveyed conventionally into apparatus 43 for labelling etc. An indexing mechanism moves the cradle in steps so that each support channel is sequentially aligned with the entry channels for transfer of syringe bodies.

The cradles and empty combs are then allowed to move onward along conveyor 41 until the leading channel of the comb is level with loading channel 46 at position Cr. The cradle is again restrained with the leading channel of the comb in alignment with loading channel 46. Syringes exiting apparatus 43 are conveyed conventionally until they reach the exit stage of loading channel in the exit stage the syringes enter 46 a holding area where they are supported by their wings on two parallel beams. Initially a first movable carrier across the channel 46 prevents syringes from exiting the loading channel. Syringes entering the exit stage are counted by breaking a light beam associated with a photodetector. When the counter finds that the loading channel contains sufficient syringes to fill one channel of a comb, a second movable barrier is moved across the loading channel to isolate the predetermined number of syringes. The syringes exiting apparatus 43 build up behind the second barrier in the channel 46 which is of sufficient length to act as a buffer zone without blocking the exit of apparatus 43.

The first barrier is now withdrawn and a pusher arm moves the isolated group of syringes out of the exit stage into the waiting channel of the comb. The completion of the pushing operation actuates the repositioning of the first movable barrier and indexing of the cradle to bring the next channel of the comb into alignment with the loading channel of the exit stage. This sequence is repeated until all the channels of the comb are filled. The loaded cradle is then released and the following cradle with an empty comb takes its place.

The loaded cradle continues to move in direction C, until it reaches transfer section 48. Here transverse belts transfer the loaded cradle to conveyor 40 where it moves in direction B towards operator position A. The operator lifts the loaded comb from the cradle and places it into a storage box for stock-piling until required for another processing operation. The operator places comb with syringe bodies is placed on the now empty cradle and it continues in direction B to repeat the whole processing cycle. As an alternative procedure, the loaded combs may continue on conveyor 41 to be taken directly to another processing station, where they may be unloaded and loaded at stations analogous to Cu and Cr.

By use of the support rack of the present invention, syringes can be loaded and unloaded more quickly and the number of breakages is reduced, so that a reduction in overall manufacturing cost is achieved. Since the syringes are returned to the comb in a more gentle manner, the process can be more fully automated, by using robots to perform the removal/reloading steps. As such, those formerly employed performing this task may be more fruitfully employed in the quality control checking of the syringes thereby increasing the rate of production of finished syringes.

I claim:

1. A storage system for articles with protruding lips or wings (4), in which the articles are suspended by their protruding parts in slots between supported arms with the protruding parts resting on the arms, characterized in that the slots (5) are defined between elongate fingers (2) connected together at one end by a spine member (12) forming a support rack (A) capable of holding more than one article in each slot, and the support rack is removable mounted on a support cradle (6) having a base (7) with primary upright posts (8,9) on which are rested the outmost fingers and/or the spine of the support rack, and secondary upright posts (11) which support the free end of each finger.

2. A storage system according to claim 1, in which a pair of primary posts (9) adjacent the secondary posts (11) are higher than a pair of primary posts (8) remote from the secondary posts, so that the rack (A) is supported at an inclined angle to the base (7) of the cradle (6).

3. A storage system according to claim 1 or 2, in which the upright posts (8, 9, 11) locate in depressions in the lower surface of the fingers (2).

4. A storage system according to claim 1, in which the rack has generally flat upper surfaces with downwardly depending edge portions.

5. A storage system for articles with protruding lips or wings (4), in which the articles are suspended by their protruding parts in slots between supported arms with the protruding parts resting on the arms, characterized in that the slots (5) are defined between elongate fingers (2) connected together at one end by a spine member (12) forming a support rack (A) capable of holding more than one article in each slot, and the support rack is removably mounted in a box having a base (50) and a cover (52), the base having an internal shelf of ledge (51) to support the peripheral edges of the rack (A), the cover having an internal projection (53) to restrain vertical movement of the rack when located on the shelf (51), and the base or cover having projections (54) which engage between the fingers (2) to prevent lateral movement thereof when the rack is located on the shelf (51).

6. A storage rack for articles with protruding lips or wings (4), for use in the storage systems of claims 1 or 5, in which the articles are suspended by their protruding parts in slots between rigid arms with the protruding parts resting on the arms, characterized in that the slots (5) are defined between elongate fingers (2) connected together at one end by a spine member (12) forming support rack (A) capable of holding more than one article in each slot, the fingers having flat upper surfaces that stand above the upper surface of the spine, so that a channel (1a) is defined between the fingers at the spine end of the rack, the lower surfaces of the fingers and spine lying in substantially the same plane, and containing depressions (10, 15) for engaging with support posts.

7. A handle for carrying a support rack as claimed in claim 6, the carrying handle comprising a grip portion (30) and at least two dependent members (23, 20) for engagement with surfaces of the support rack so that the support rack can be lifted using the grip portion.

8. A carrying handle according to claim 7, wherein at least one of the dependent members is movable, by a pivoting or sliding motion relative to the grip portion, between a first position where it engages the support rack, and a second position where it is out of engagement with the support rack.

9. Apparatus for transferring syringes to or from a storage system as claimed in claim 1 comprising:

a loading channel for receiving syringes from or for a processing operation, means for transporting the support cradle and removable support rack to a position where an end channel of the support rack is in alignment with the loading channel, means for urging syringes from the loading channel into the support rack channel or vice versa, means for indexing the support cradle to bring the next free support rack channel in to alignment with the loading channel.

10. Apparatus according to claim 9 comprising:

a loading channel for receiving syringes exiting from a processing operation, means for counting syringes entering the channel, means for preventing syringes leaving the channel until a predetermined number of syringes are in the channel, means for preventing syringes entering the loading channel after a predetermined number of syringes are in the channel, means for urging the predetermined number of syringes from the loading channel to the support rack channel.

11. Apparatus for transporting a storage system as claimed in claim 1, comprising a pair of conveyors which in operation transport support cradles in opposite directions, a pair of transfer sections which in operation work in opposite directions to transfer support cradles between the conveyors, one conveyor having position-detecting means to locate and hold conveyed assemblies in support cradles with the support rack in alignment with loading channels for transferring syringes to and from a processing machine and indexing means for sequentially aligning channels of the support rack on a cradle with the loading channels.

* * * * *